United States Patent [19]

Philippe et al.

[11] Patent Number: 5,587,169

[45] Date of Patent: Dec. 24, 1996

[54] COSMETIC OR PHARMACEUTICAL COMPOSITION COMPRISING AN ALKYL CARBAMATE AS HYDRATING AGENT

[75] Inventors: Michel Philippe, Wissous; Didier Semeria, Courtry; Eric Bollens, Saint Maurice, all of France

[73] Assignee: L'Oréal, Paris, France

[21] Appl. No.: 421,065

[22] Filed: Apr. 13, 1995

[30] Foreign Application Priority Data

Apr. 13, 1994 [FR] France .................................. 94 04377

[51] Int. Cl.⁶ .............................. A61K 7/48; A61K 7/50; A61K 7/075
[52] U.S. Cl. ..................... 424/401; 424/70.31; 514/561
[58] Field of Search ................................ 424/401, 70.31; 514/561

[56] References Cited

U.S. PATENT DOCUMENTS

| | | |
|---|---|---|
| 2,040,997 | 5/1936 | Johnson . |
| 2,808,402 | 10/1957 | Boettner . |
| 4,382,765 | 5/1983 | Moller et al. . |
| 5,230,890 | 7/1993 | Philippe et al. .................. 424/401 |
| 5,354,510 | 10/1994 | Vanlerberghe et al. . |

FOREIGN PATENT DOCUMENTS

| | | |
|---|---|---|
| 0543132 | 12/1955 | Belgium . |
| 0577506 | 1/1994 | European Pat. Off. . |
| 2379283 | 9/1978 | France . |
| 2703993 | 10/1994 | France . |

*Primary Examiner*—Nathan M. Nutter
*Attorney, Agent, or Firm*—Finnegan, Henderson, Farabow, Garrett & Dunner

[57] ABSTRACT

The invention relates to a cosmetic or pharmaceutical composition comprising as hydrating agent a compound of the alkyl N-(hydroxyalkyl)carbamate family.

13 Claims, No Drawings

COSMETIC OR PHARMACEUTICAL COMPOSITION COMPRISING AN ALKYL CARBAMATE AS HYDRATING AGENT

The present invention relates to a cosmetic or pharmaceutical composition comprising as hydrating agent an alkyl N-(hydroxyalkyl)carbamate.

The compounds of the following general formula (I) are known:

$$R_1-CH(R_2)-CH_2-O-C(=O)-N(R_3)-A \quad (I)$$

in which:

$R_1$ represents an alkyl or alkenyl radical having 4–18 carbon atoms, $R_2$ represents an alkyl or alkenyl radical having 2–16 carbon atoms, $R_3$ represents a hydrogen atom or an alkyl radical having 1–6 carbon atoms, and A represents a nonionic hydrophilic group, preferably a nonionic hydroxylated group.

These compounds may be obtained by reacting, in a solvent, an amino alcohol of formula $R_3$—NH—A with a compound of formula (II):

$$R_1-CH(R_2)-CH_2-O-C(=O)-X \quad (II)$$

$R_1$, $R_2$, $R_3$ and A having the same meanings as those given above and X representing a halogen atom, in particular a chlorine atom, or a radical derived from a 5-membered nitrogen-containing heterocycle, in particular a radical originating from an imidazole such as the one of formula (III):

$$-N\text{(imidazole)} \quad (III)$$

As a solvent, dichloromethane, 1,2-dichloroethane, 1,1,1-trichloroethane, chloroform, acetonitrile, toluene, dioxane, tetrahydrofuran, 1,2-dimethoxyethane, cyclohexane, water or a mixture of these solvents may be used.

The reaction is performed at a temperature of between $-5°$ C. and $50°$ C., and preferably below $10°$ C.

The reaction may be performed in the presence of a base. The latter may be chosen from alkali metal or alkaline-earth metal hydroxides, sodium hydrogen carbonate, alkali metal alcoholates, alkali metal hydrides and tertiary amines such as pyridine or triethylamine.

Among the compounds corresponding to the general formula (I), the following may be mentioned in particular:

N-(2-ethylhexyloxycarbonyl)-N-methyl-D-glucamine,

N-(2-butyloctyloxycarbonyl)-N-methyl-D-glucamine,

N-(2-decyltetradecyloxycarbonyl)-D-glucamine,

N-(2-hexyldecyloxycarbonyl)-D-glucamine,

3-[N-(2-decyltetradecyloxycarbonyl)amino]-1,2-propanediol,

2-[N-(2-decyltetradecyloxycarbonyl)amino]-2-hydroxymethyl-1,3-propanediol, and

2-[N-(2-hexyldecyloxycarbonyl)amino]-1-ethanol.

It was found that, surprisingly, the compounds of formula (I) display advantageous cosmetic properties, especially skin-hydrating properties.

It was, in effect, found to be possible, by applying these products to the skin, to decrease the loss of water therefrom and/or increase the binding of water in the stratum corneum. These compounds may hence be used as hydrating agents, in particular for the skin, in humans. They make it possible to retain or restore the suppleness of the skin, its elasticity, its resistance to body movements and its function as a barrier to the entry of toxic substances.

The subject of the present invention is hence a composition, in particular a cosmetic or pharmaceutical composition, comprising at least one hydrating agent of the formula (I). A second subject of the invention is the use of a compound of formula (I) as hydrating agent in a composition, in particular a cosmetic or pharmaceutical composition.

In the compound of formula (I) according to the invention, the radical $R_1$ can represent an alkyl radical having from 4 to 14 carbon atoms, $R_2$ can represent an alkyl radical having from 2 to 12 carbon atoms and $R_3$ can represent a hydrogen atom or a methyl radical.

Preferably, A represents a radical $-(CH_2)_n-(CHOH)_m-Z$, in which n represents an integer equal to 0 or 1, m represents an integer from 0 to 5 and Z is a monohydroxylated or polyhydroxylated alkyl radical having from 1 to 4 carbon atoms.

In particular, Z is chosen from the group comprising the following radicals:

$-CH_2OH$, $-CH_2-CH_2OH$, $-CH(CH_2OH)_2$, $-C(CH_2OH)_3$, $-C(CH_2OH)_2(CH_3)$, $-CH(CH_3)-CH_2OH$, and $-C(CH_3)_2-CH_2OH$.

The cosmetic composition according to the invention generally comprises, in addition to the hydrating agent according to the invention, a cosmetically acceptable vehicle such as water; organic solvents compatible with a cutaneous application such as acetone, isopropanol and ethanol; triglycerides of fatty acids containing 6–24 carbon atoms, glycol ethers, polyalkylene glycol esters and volatile silicones.

The cosmetic composition according to the invention preferably comprises 0.001 to 15% by weight of compound of formula (I) relative to the total weight of the composition.

The composition according to the invention can also contain conventional cosmetic additives such as fats, in particular natural or synthetic oils; thickening or gelling agents such as cellulose or its derivatives, acrylic polymers, alginates, gums, polyethylene glycols, bentonites and montmorillonites; humectants such as glycerol and triacetin; antioxidants; preservatives.

The composition according to the invention can take the form of an aqueous lotion, a gel, an emulsion, a cream or a foam to be applied to the skin. It can also take the form of a vesicular dispersion of ionic or nonionic lipids, it then being possible for the said vesicles to serve as encapsulating agent for lipophilic or hydrophilic active ingredients such as retinoic acid or UV screening agents.

The said composition may be used as a skin care product and/or make-up product, especially as a skin care or sun cream, make-up foundation and/or blusher or eyeshadow.

The invention is illustrated in greater detail in the examples which follow, in which the percentages are given by weight except where otherwise stated.

Examples 1 to 7 describe a method of preparation of seven particular compounds according to the invention, and Examples 8 to 12 illustrate the hydrating properties of the compounds according to the invention and formulations of cosmetic compositions containing them.

Before these, the two methods employed for evaluating the action of the compounds as skin-hydrating agents are described.

A) Measurement of imperceptible water loss (IWL)

This measurement was performed using an evaporimeter (Servomed) which determines quantitatively the evaporation of water, i.e., a transport of water by diffusion, from a sample of stratum corneum enclosing a cylindrical capsule containing water, the whole being placed in a chamber at controlled temperature and relative humidity.

Sensors enabled the water vapour partial pressure to be measured at two points located at different distances from the sample.

The gradient of water vapour partial pressure between the two points was determined in this way, and hence the rate of evaporation in accordance with Fick's law.

B) Measurement of skin conductivity

This measurement enabled changes in the degree of hydration of the skin to be demonstrated.

It was performed using an apparatus containing a central electrode in the form of a rod surrounded by a cylindrical electrode.

The apparatus was applied to the skin, and a high frequency alternating current was applied.

It was found that, the greater the hydration of the skin, the higher the amount of current consumed.

The increase in conductivity of the skin, and hence the increase in its degree of hydration, were thus demonstrated.

EXAMPLE 1

Preparation of N-(2-ethylhexyloxycarbonyl)-N-methyl-D-glucamine

In a reactor, 117 g (0.6 mol) of N-methyl-D-glucamine were dissolved in a mixture of 800 ml of water and 400 ml of tetrahydrofuran, and 201.6 g (2.4 mol) of sodium hydrogen carbonate were then dispersed. While the temperature of the reaction mixture was maintained at 5° C., 115.6 g (0.6 mol) of 2-ethylhexyl chloroformate were added dropwise, and the mixture was then allowed to react for 3 hours with stirring at 5° C. and left standing overnight at room temperature. The reaction mixture was then filtered and concentrated; the pasty residue obtained was dissolved in 2 liters of acetone and then filtered after cooling to 5° C. The crystallized product collected was dried. 105 g (50% yield) of N-(2-ethylhexyloxycarbonyl)-N-methyl-D-glucamine, the melting point of which is 74° C., were obtained.

EXAMPLE 2

Preparation of N-(2-butyloctyloxycarbonyl)-N-methyl-D-glucamine

The compound was prepared according to the same procedure as in Example 1, using:

78 g (0.4 mol) of N-methyl-D-glucamine
134.4 g (1.6 mol) of sodium bicarbonate
99.4 g (0.4 mol) of 2-butyloctyl chloroformate.

62 g of N-(2-butyloctyloxycarbonyl)-N-methyl-D-glucamine were obtained in the form of a white powder, the melting point of which was 77° C.

EXAMPLE 3

Preparation of N-(2-decyltetradecyloxycarbonyl)-D-glucamine

In a 1000 ml reactor, 36.2 g of D-glucamine were solubilized in 100 ml of water. 135 ml of tetrahydrofuran were added, followed by 67.2 g of sodium bicarbonate. With stirring, the mixture was brought to −2° C. and 83.3 g of 2-decyltetradecyl chloroformate were then added dropwise. When the addition was complete, the mixture was left for two hours at 0° C. and then allowed to return gradually, also in the course of two hours, to 25° C. The insoluble matter was removed on a sinter and the solution was then concentrated to dryness on a rotary evaporator. The residue was recrystallized in one liter of acetone, and this operation was repeated once in one liter of acetone and then once in one liter of ethyl acetate/acetone mixture.

61 g of N-(2-decyltetradecyloxycarbonyl)-D-glucamine were obtained in the form of a white powder, the melting point of which was 82° C.

EXAMPLE 4

Preparation of N-(2-hexyldecyloxycarbonyl)-D-glucamine

The compound was prepared according to the same procedure as in Example 3, using:

46.8 g (0.24 mol) of D-glucamine,
80.6 g (0.96 mol) of sodium bicarbonate,
73.08 g (0.24 mol) of 2-hexyldecyl chloroformate.

70 g of N-(2-hexyldecyloxycarbonyl)-D-glucamine were obtained in the form of a white powder, the melting point of which was 81° C.

EXAMPLE 5

Preparation of 3-[N-(2-decyltetradecyloxycarbonyl) amino]-1,2-propanediol

The compound was prepared according to the procedure of Example 3, using:

18.2 g (0.2 mol) of 3-amino-1,2-propanediol,
67.2 g (0.8 mol) of sodium bicarbonate,
83.3 g (0.2 mol) of 2-decyltetradecyl chloroformate.

95 g of an amber-coloured oil were obtained, which product was purified on silica using dichloromethane/methanol mixtures (from 10:0 to 9:1 vol/vol).

80 g of a white wax were obtained, the purity of which was monitored by thin-layer chromatography (eluent: dichloromethane/methanol, 95:5 vol/vol; Rf=0.34).

EXAMPLE 6

Preparation of 2-[N-(2-decyltetradecyloxycarbonyl) amino]-2-hydroxymethyl-1,3-propanediol The compound was prepared according to the procedure of Example 3, using:

24.2 g (0.2 mol) of tris(hydroxymethyl)aminomethane,
67.2 g (0.8 mol) of sodium bicarbonate,
83.3 g (0.2 mol) of 2-decyltetradecyl chloroformate.

After reaction and purification on silica (eluent: heptane/ethyl acetate, 7:3 then 6:4 vol/vol), 40 g of a white wax were obtained, the melting point of which was 51° C. and the purity of which was verified by thin-layer chromatography (dichloromethane/methanol, 9:1 vol/vol; Rf=0.45).

EXAMPLE 7

Preparation of 2-[N-(2-hexyldecyloxycarbonyl)amino-1-ethanol 105.3 g of carbonyldiimidazole (0.65 mol) were solubilized in 1200 ml of dichloromethane. 133.38 g (0.55 mol) of 2-hexyldecanol were then added dropwise over 1 hour at 20° C. The mixture was left stirring for 4 hours at 20° C. The reaction mixture was poured into a separating funnel and washed 4 times with 200 ml of water. The organic phase was dried over sodium sulphate and then concentrated to dryness.

173 g of 2-(hexyldecyloxycarbonyl)imidazole were then obtained in the form of a yellow oil.

12.2 g (0.2 mol) of aminoethanol were solubilized in 400 ml of anhydrous tetrahydrofuran. A solution of 73.9 g (0.22 mol) of 2-(hexyldecyloxycarbonyl)imidazole in 300 ml of tetrahydrofuran was then added at 20° C. over 90 minutes.

Stirring was continued for 24 hours at 20° C. and the mixture was then evaporated to dryness. 88 g of an oil were obtained, which product was solubilized in 500 ml of ethyl acetate and then washed three times with 100 ml of water. The organic phases were combined, dried over sodium sulphate and then evaporated to dryness.

71 g of an amber-coloured oil were obtained, which product was purified on silica (eluent: heptane/ethyl acetate, 9:1 then 8:2 vol/vol) to yield 35 g of a colourless oil, the purity of which was monitored by thin-layer chromatography ( eluent: ethyl acetate/heptane, 5:5 vol/vol; Rf=0.55).

EXAMPLE 8

The compounds of Examples 2, 3, 4, 6 and 7 were prepared in the proportion of 3% in isopropanol and then applied to pieces of delipidized stratum corneum. 20 hours after the application, the imperceptible water loss (IWL) was measured for each compound.

The following results were obtained:

| Compound | 2 | 3 | 4 | 6 | 7 |
| --- | --- | --- | --- | --- | --- |
| IWL | −6 +/− 1 | −26 +/− 7 | −25 +/− 2 | −29 +/− 3 | −8 +/− 2 |

Hence it was seen that the application of the compounds according to the invention enabled the evaporation of the water contained in the stratum corneum to be reduced significantly.

EXAMPLE 9

The compounds of Examples 1, 3, 4, 5 and 6 were prepared in the proportion of 3% in isopropanol, and then applied to pieces of delipidized stratum corneum. 20 hours after the application, the conductivity of the stratum corneum was measured for each compound.

The following results were obtained:

| | Compound | | | | |
| --- | --- | --- | --- | --- | --- |
| | 1 | 3 | 4 | 5 | 6 |
| Conductivity | 37 +/− 15 | 60 +/− 25 | 41 +/− 7 | 43 +/− 6 | 65 +/− 8 |

It was seen that the conductivity of the skin was increased when treated with the compounds according to the invention. Hence these compounds did indeed enable the degree of hydration of the skin to be increased.

EXAMPLE 10

Comparative Example

A conductivity measurement was performed on two pieces of non-delipidized stratum corneum, to which the compound was applied at a concentration of 3% in isopropanol and which were left to stand for 20 hours.

This measurement was performed for a) 2-[N-(2-decyltetradecyloxycarbonyl)amino]-2-hydroxymethyl-1,3-propanediol (compound of Example 6), and b) 2-[N-(2-decyltetradecanoyl)amino]-2-hydroxymethyl-1,3-propanediol, known to be a hydrating agent.

The following results were obtained:

| | Conductivity |
| --- | --- |
| Compound a) according to the invention | 23 +/− 4 |
| Compound b), comparative | not significant |

The compound according to the invention hence enabled the degree of hydration of the skin to be increased more significantly than the compound of the prior art, which was, however, known to be a hydrating agent.

EXAMPLE 11

A day cream for the face having the following composition was prepared:

| | |
| --- | --- |
| cetyl alcohol | 2.5% |
| sorbitan tristearate | 0.9% |
| poly(ethylene oxide) stearate | 2% |
| (polyoxyethylenated 40 times) | |
| glyceryl stearate | 3% |
| myristyl myristate | 2% |
| hydrogenated polyisobutene | 2.5% |
| octyl palmitate | 4% |
| polydimethylsiloxane (10 $cm^2 \cdot s$) | 5% |
| apricot-kernel oil | 5.7% |
| N-(2-decyltetradecyloxycarbonyl)-D- | 0.5% |
| glucamine | 0.5% |
| preservatives | 0.5% |
| water | qs 100% |

A day cream was obtained which took the form of an emulsion enabling the skin to be well covered and protected, and which was especially suitable for normal and dry skins.

EXAMPLE 12

A night cream having the following formulation was prepared:

| | |
|---|---|
| mixture of glyceryl mono- and distearates and of poly(ethylene oxide) stearate | 2% |
| 2-[N-(2-decyltetradecyloxycarbonyl)amino-2-hydroxymethyl-1,3-propanediol | 3% |
| apricot-kernel oil | 17% |
| cyclopentadimethylsiloxane | 1.5% |
| carbomer (sold under the brand name CARBOPOL) | 0.75% |
| preservatives | 0.5% |
| triethanolamine | 0.75% |
| water | qs 100% |

A night cream was obtained which took the form of a thick, shiny emulsion very gentle to apply and which proved nourishing and hydrating to the skin, especially for dry skins.

We claim:

1. A cosmetic or pharmaceutical composition comprising at least one hydrating agent corresponding to the formula (I):

$$R_1-\underset{R_2}{\underset{|}{CH}}-CH_2-O-\overset{O}{\overset{\|}{C}}-\underset{R_3}{\underset{|}{N}}-A \quad (I)$$

wherein:

- $R_1$ represents an alkyl or alkenyl radical having from 4 to 18 carbon atoms,
- $R_2$ represents an alkyl or alkenyl radical having from 2 to 16 carbon atoms,
- $R_3$ represents a hydrogen atom or an alkyl radical having from 1 to 6 carbon atoms, and
- A represents a nonionic hydroxylated group.

2. A composition according to claim 1, wherein $R_1$ represents an alkyl radical having from 4 to 14 carbon atoms, $R_2$ represents an alkyl radical having from 2 to 12 carbon atoms, and $R_3$ represents a hydrogen atom or a methyl radical.

3. A composition according to claim 1, wherein A represents a radical $-(CH_2)_n-(CHOH)_m-Z$, in which n represents an integer equal to 0 or 1, m represents an integer from 0 to 5 and Z is a monohydroxylated or polyhydroxylated alkyl radical having from 1 to 4 carbon atoms.

4. A composition according to claim 3, wherein Z represents a hydroxylated radical selected from the following radicals:

$$-CH_2OH, \ -CH_2-CH_2OH, \ -CH(CH_2OH)_2,$$

$$-C(CH_2OH)_3, \ -\underset{CH_3}{\underset{|}{C}}(CH_2OH)_2, \ -\underset{CH_3}{\underset{|}{CH}}-CH_2OH, \text{ and}$$

$$-\underset{CH_3}{\overset{CH_3}{\underset{|}{\overset{|}{C}}}}-CH_2OH.$$

5. A composition according to claim 1, wherein the compound of the formula (I) is selected from:

N-(2-ethylhexyloxycarbonyl)-N-methyl-D-glucamine,
N-(2-butyloctyloxycarbonyl)-N-methyl-D-glucamine,
N-(2-decyltetradecyloxycarbonyl)-D-glucamine,
N-(2-hexyldecyloxycarbonyl)-D-glucamine,
3-[N-(2-decyltetradecyloxycarbonyl)amino]-1,2-propanediol,
2-[N-(2-decyltetradecyloxycarbonyl)amino]-2-hydroxymethyl-1,3-propanediol, and
2-[N-(2-hexyldecyloxycarbonyl)amino]-1-ethanol.

6. A composition according to claim 1, wherein the compound of the formula (I) is present at a concentration of from 0.001 to 15% by weight relative to the total weight of the composition.

7. A composition according to claim 1, wherein said composition is a skin care product.

8. A composition according to claim 7, wherein said skin care product is a skin cream.

9. A composition according to claim 1, wherein said composition is a make-up product.

10. A composition according to claim 9, wherein said make-up product is a make-up foundation, a blusher, or an eyeshadow.

11. A method of treatment of the skin, comprising the step of applying to the skin a cosmetic or pharmaceutical composition, wherein said composition comprises at least one hydrating agent corresponding to formula (I):

$$R_1-\underset{R_2}{\underset{|}{CH}}-CH_2-O-\overset{O}{\overset{\|}{C}}-\underset{R_3}{\underset{|}{N}}-A \quad (I)$$

in which:

- $R_1$ represents an alkyl or alkenyl radical having from 4 to 18 carbon atoms,
- $R_2$ represents an alkyl or alkenyl radical having from 2 to 16 carbon atoms,
- $R_3$ represents a hydrogen atom or an alkyl radical having from 1 to 6 carbon atoms, and
- A represents a nonionic hydroxylated group.

12. A method of hydrating the skin, comprising the step of applying to the skin the cosmetic or pharmaceutical composition, wherein said composition comprises at least one hydrating agent corresponding to formula (I):

$$R_1-\underset{R_2}{\underset{|}{CH}}-CH_2-O-\overset{O}{\overset{\|}{C}}-\underset{R_3}{\underset{|}{N}}-A \quad (I)$$

in which:

- $R_1$ represents an alkyl or alkenyl radical having from 4 to 18 carbon atoms,
- $R_2$ represents an alkyl or alkenyl radical having from 2 to 16 carbon atoms,
- $R_3$ represents a hydrogen atom or an alkyl radical having from 1 to 6 carbon atoms, and
- A represents a nonionic hydroxylated group.

13. A method of formulating a cosmetic or pharmaceutical composition comprising the steps of:

selecting an agent for the purpose of hydrating skin, said agent corresponding to formula (I):

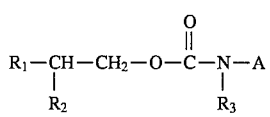

(I)

in which:

R$_1$ represents an alkyl or alkenyl radical having from 4 to 18 carbon atoms,

R$_2$ represents an alkyl or alkenyl radical having from 2 to 16 carbon atoms,

R$_3$ represents a hydrogen atom or an alkyl radical having from 1 to 6 carbon atoms, and A represents a nonionic hydroxylated group, and formulating a cosmetic or pharmaceutical composition inlcuding said selected agent.

* * * * *